United States Patent [19]

Hickam

[11] 4,101,277

[45] Jul. 18, 1978

[54] DETECTION OF INCIPIENT FAULTS IN HYDROGEN-COOLED GENERATORS

[75] Inventor: William M. Hickam, Churchill, Pa.

[73] Assignee: Westinghouse Electric Corp., Pittsburgh, Pa.

[21] Appl. No.: 732,631

[22] Filed: Oct. 15, 1976

[51] Int. Cl.² .............................................. G01N 31/00
[52] U.S. Cl. ............................... 23/232 R; 23/254 R; 73/23
[58] Field of Search .................... 73/23, 19; 23/232 R, 23/232 E, 254 R, 254 E; 361/35, 37

[56] References Cited

U.S. PATENT DOCUMENTS

| 3,566,673 | 3/1971 | Kogan | 73/23 |
| 3,680,359 | 8/1972 | Lynch | 73/23 |
| 3,866,460 | 2/1975 | Pearce | 73/19 |

*Primary Examiner*—Richard C. Queisser
*Assistant Examiner*—Stephen A. Kreitman
*Attorney, Agent, or Firm*—G. H. Telfer

[57] ABSTRACT

A method and apparatus are disclosed for the detection of incipient faults in large hydrogen-cooled dynamoelectric machines such as turbine generators. Such machines operate in a hydrogen atmosphere, for cooling, and unavoidably contain some air. The heating of organic insulation, or of metallic parts of the machine, associated with incipient faults results in oxidation or other reactions that reduce the amount of free oxygen present in the machine atmosphere. The occurrence of such incipient faults is detected by monitoring the oxygen content to detect any substantial reduction in the concentration of free oxygen. Since the amount of air in the machine may vary, it is preferred to monitor the oxygen content by determining the ratio of nitrogen to oxygen in the machine.

8 Claims, 2 Drawing Figures

DETECTION OF INCIPIENT FAULTS IN HYDROGEN-COOLED GENERATORS

BACKGROUND OF THE INVENTION

The present invention relates to the detection of incipient faults in dynamoelectric machines and especially large hydrogen-cooled machines such as turbine generators.

Various fault or abnormal conditions may occur in dynamoelectric machines such as partial or complete insulation failures, partial or complete breakage of conductors, local overheating or metallic parts of the machine such as the stator core, and others. If such conditions are not detected until a complete failure or other serious damage actually occurs, the machine may be badly damaged by excessive temperatures or by arcing or flashovers which may occur, and which may result in complete or catastrophic failure of the machine. At the very least, the occurrence of a serious fault may require extensive repairs such as partial or complete rewinding or rebuilding of parts of the machine, resulting in an extended shutdown of the machine and heavy expense.

It is desirable therefore to detect incipient faults before they can develop into complete failures, so that the trouble can be remedied before it causes serious damage. Most faults of this kind are associated with overheating and abnormal temperature rise has been utilized to indicate the presence of a fault or other problem. Temperature detectors in the stator slots or large machines have been used for many years to detect overtemperature but such detectors respond only to overheating of the conductors themselves such as may be caused by excessive conductor currents or by a failure of the ventilation system.

More recently, incipient thermal fault detectors have come into use which monitor the changes in concentration of particulate matter in the circulating hydrogen atmosphere of the machine. These systems are based on the fact that most organic insulating materials used in large generators give off particulate matter when heated and an increase in the concentration of particulates is thus a signal that overheating is occurring. This type of system, however, has several disadvantages. Most organic insulating materials exhibit particulation signals when the temperature reaches approximately 200° C. The typical hydrogen gas temperature in a generator during operation, however, is approximately 60° C. In order for the insulation to reach the necessary surface temperature, therefore, the temperature of the conductor itself must become very high before enough heat is conducted through the thick, high-voltage insulation. It has been shown by tests, for example, that copper conductors with usual insulation must reach a temperature of 600° C before particulation occurs at the surface of the insulation. Fault detectors responsive to lower conductor temperatures would, therefore, be highly desirable. Fault detection by particulate concentration, furthermore, indicates only overheating of organic components, such as the surface layers of conductor insulation, and does not provide any direct indication of conductor temperatures or of overheated components other than organic insulation, such as metallic parts of the generator including the stator core. Such detectors are responsive only to temperature and do not meet the need for detecting arcing and corona faults which cause only very localized heating of the metal parts such as conductors.

Another disadvantage of the use of organic particulation for detecting thermal faults is the doubtful particulation life of organic materials at constant temperature. Tests indicate that the temperature at which particulation occurs increases with particulation time, and that particulation ceases to occur after some time period when the material is held at a constant temperature. Sustained and reproducible particulation signals are thus difficult to achieve under conditions of actual use. It has been attempted to overcome this problem by means of sacrificial coatings on the surface of organic insulation which would have lower particulation temperatures than the usually used materials. Such coatings, however, in addition to increasing the cost, usually possess only a limited particulation time at constant temperature.

SUMMARY OF THE INVENTION

The present invention provides a method for detecting incipient faults in large generators which does not depend solely on thermally-induced effects in the organic insulation. Large generators of the type for which fault protection is desired are hydrogen cooled, and for this purpose have a substantially gas-tight housing filled with hydrogen which is circulated through the housing during operation of the machine. In actual practice, some air is always unavoidably present in the machine mixed with the hydrogen and may amount to as much as 10% of the gas mixture in the machine. Thus, a substantial amount of free oxygen is present as a component of the gas. The hydrogen and oxygen in the machine can react to form water vapor at temperatures as low as 100° C, the reaction being catalyzed by the copper and copper oxide present in the machine, and the heated copper and other metals, as well as the organic materials present, also react with the oxygen at relatively low temperature to form oxides or other compounds. The occurrence of elevated temperatures in any part of the machine, therefore, either of the insulation or of metal components, results in oxidation or other reactions and has the effect of removing some of the free oxygen from the gas mixture in the machine. By monitoring the oxygen concentration, therefore, the occurrence of such temperatures can be detected by a substantial decrease in oxygen concentration which indicates the presence of an incipient fault.

The air in the machine is present as a result of leakage into the housing and the amount of air mixed with the hydrogen changes from time-to-time. Instead of monitoring the amount of free oxygen directly, therefore, it is preferred to monitor the ratio of nitrogen to oxygen which remains substantially constant irrespective of the amount of air as long as no oxidation reactions are occurring. A substantial increase in the ratio of nitrogen to oxygen, however, indicates a reduction in the amount of oxygen and thus indicates the appearance of an overtemperature. The nitrogen-to-oxygen ratio can be determined directly or can be determined by measuring the amount of air in the machine and the oxygen content which should have a constant ratio under normal conditions.

BRIEF DESCRIPTION OF THE DRAWING

The invention will be more fully understood from the following detailed description, taken in connection with the accompanying drawings, in which.

DESCRIPTION OF THE PREFERRED EMBODIMENT

Figure 2:
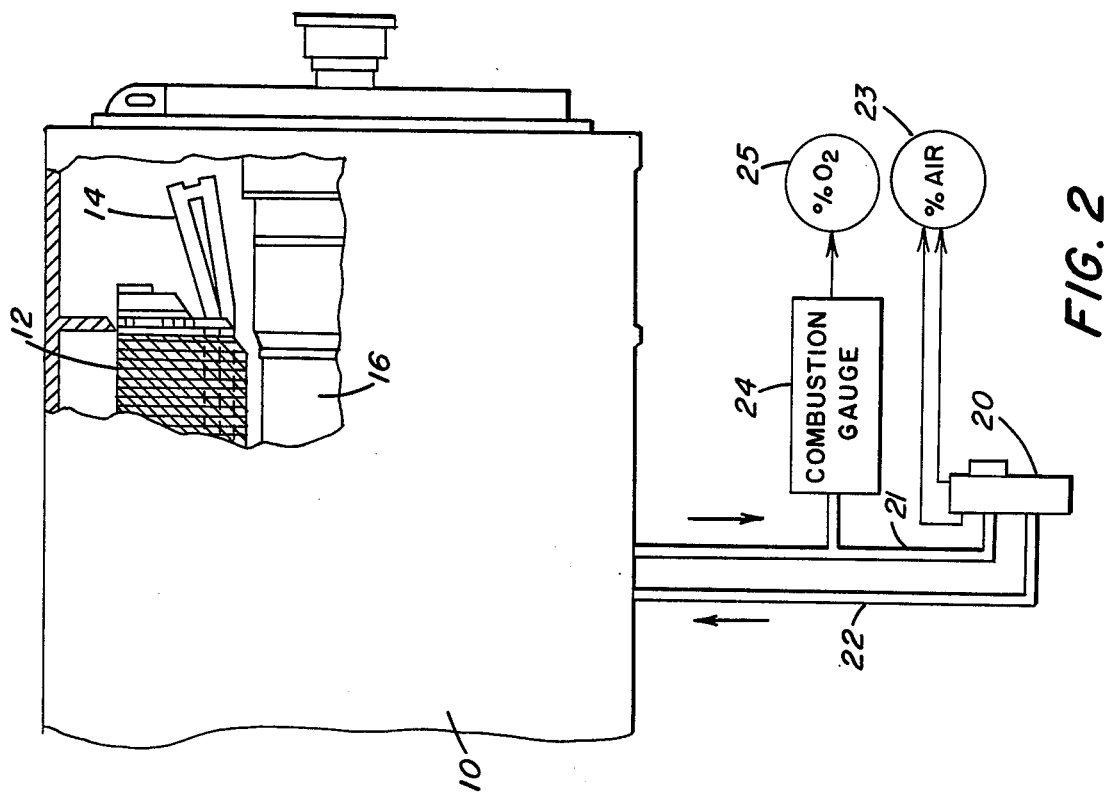
FIG. 2 is a somewhat diagrammatic view illustrating a fault detection system embodying the present invention.

As previously indicated, the invention is particularly intended for the detection of incipient faults in large, hydrogen-cooled turbine generators. The machine shown for the purpose of illustration in FIG. 2 has an outer gas-tight housing 10 completely enclosing the machine. The generator has a laminated stator core 12 which carries the armature winding 14, and a rotor 16 carrying the field winding is supported in bearings in the ends of the housing 10. The winding 14 consists of stranded copper conductors covered with relatively thick high-voltage insulation consisting generally of mica or glass tapes impregnated with suitable organic resins. The housing 10 is filled with hydrogen which serves as a coolant gas to remove the heat generated in the machine and which is continuously circulated through the housing and through coolers during operation of the machine.

As previously mentioned, such a machine is subject to the occurrence of various types of faults such as insulation failure, corona discharges in the slots of the stator core or in voids in the insulation of the windings, overheating of particular elements of the machine for various reasons, broken strands in the copper conductors which may result in continuous or intermittent arcing with vibration of the conductor, and various other possible faults. Most of the faults of particular concern are associated to some degree with overheating in their incipient stages, that is, the nature of the fault is such that excessive or abnormal heating occurs at the site of the fault. The present invention makes use of this fact to provide a sensitive and accurate thermal fault detection system which is more accurate and reliable than the systems heretofore proposed.

The hydrogen with which the housing is filled is kept as pure as possible but in actual practice a certain amount of air is always mixed with the hydrogen. This is due to unavoidable leakage, release of air carried into the machine in solution in seal oil or bearing lubricants, and other causes. The amount of air thus mixed with the hydrogen is kept at not more than 10%, for safety reasons, and in many cases the nominal percentage of air is of the order of 5%. The normal composition of air is 78.03%, $N_2$, 20.99% $O_2$, 0.94% A and 0.03% $CO_2$, so that even if the air content is of the order of 5% or less, a substantial amount of free oxygen is present in the gas mixture in the generator. Hydrogen and oxygen can react to form water vapor, and copper and copper oxide are known to catalyze this reaction at temperatures as low as 100°–200° C. Certain other metals, such as nickel and platinum, have similar catalytic properties and many metallic oxides also have this property. Heated metal, such as copper and steel, reacts directly with oxygen to form oxides. Many of the organic materials present in a generator also react with oxygen at relatively low temperatures, such as 150°–175° C, to form oxides and possibly other compounds. The occurrence of abnormal temperatures of metallic parts of a generator or of the organic insulating materials in the generator, therefore, results in oxidation, or other reactions with the oxygen present, which reduces the amount of free oxygen in the gas mixture in the generator. The presence of an incipient fault of any type which causes overheating of any part or component of the generator in the temperature range of 100°–200° C, therefore, can be detected by monitoring the amount of oxygen in the gas mixture in the generator. This may be done by any known or available means for measuring oxygen concentration, and a substantial decrease in oxygen concentration is thus an indication of the occurrence of an incipient fault. Appropriate action can then be taken before a serious or major fault develops.

The air contained in the generator atmosphere is present as a result of leakage and the amount of air, and the oxygen concentration may, therefore, change from time-to-time due to additional leakage or to the addition of pure hydrogen to reduce the percentage of air. Since the concentration of oxygen in the generator atmosphere changes in this way, it is preferred to measure the ratio of oxygen to another component of the air to determine significant decreases in oxygen content. This ratio will remain constant as long as no oxygen is removed by reactions of the type discussed above, and is independent of the actual amount of oxygen. The ratio of oxygen to either nitrogen or argon can be used for this purpose as both are relatively inert under the conditions existing in a generator and the ratio remains substantially constant under normal conditions. Nitrogen is present in much larger amounts than argon so that the nitrogen-oxygen ratio is more easily and accurately measured and equipment is readily available for making such determinations.

Figure 1:
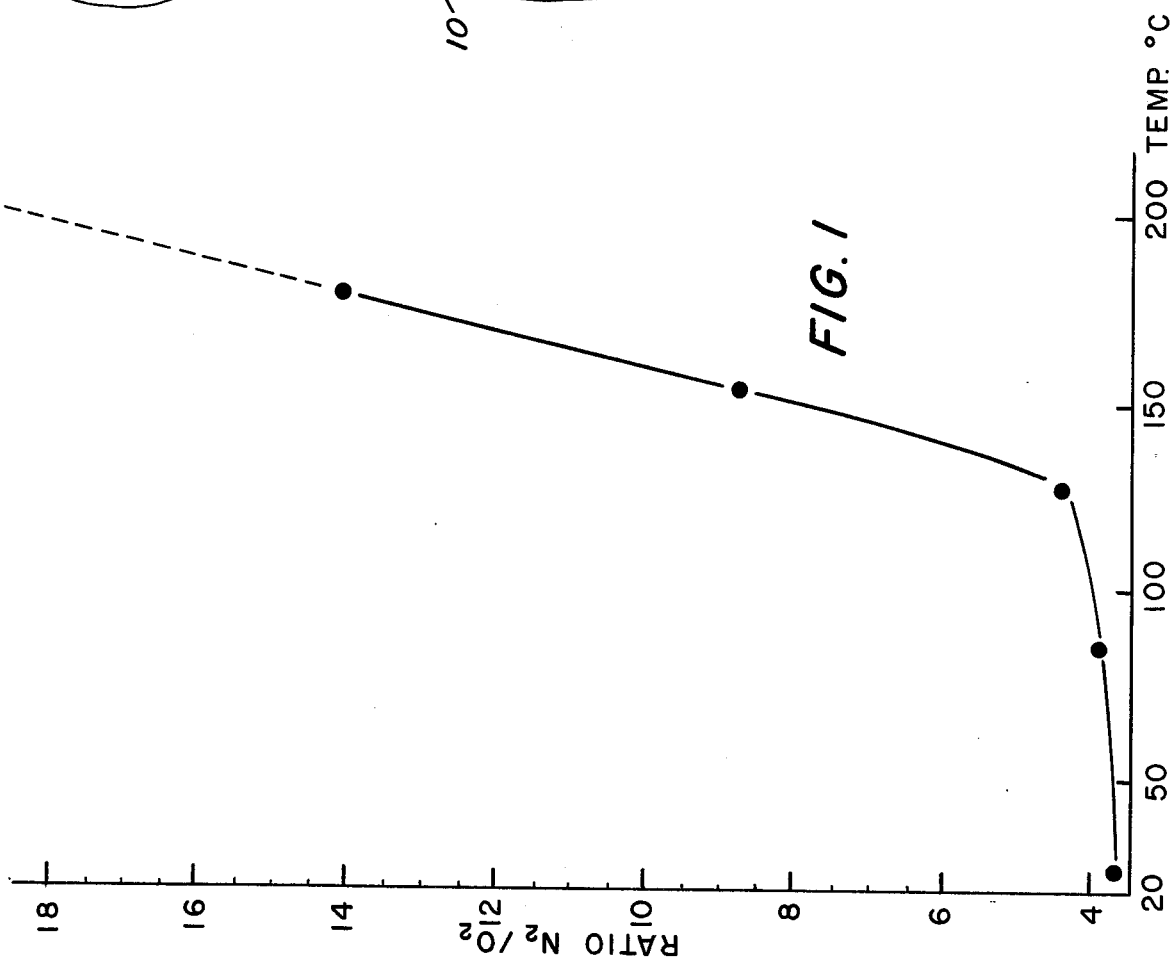
FIG. 1 is a curve illustrating the effect of heating copper in a typical generator atmosphere.

The effectiveness of the nitrogen-oxygen ratio as an indication of heating is shown by the test results illustrated in FIG. 1. This figure shows the results of measuring the nitrogen-oxygen ratio in a typical generator atmosphere of 96.6% hydrogen and 3.4% air at atmospheric pressure. Copper samples were heated in this atmosphere and the nitrogen-oxygen ratio determined for various temperatures of the samples. It will be seen that at about 120° C, the ratio starts to rise quite rapidly, indicating that at and above this temperature the oxygen was reacting with the heated copper so that the amount of free oxygen rapidly decreased. An accurate and sensitive indication of the copper temperature is thus provided. This effect has been confirmed by observation of many gas samples taken from actual generators in regular commercial service. In all cases, the nitrogen-to-oxygen ratio was the normal ratio for air (slightly less than 4.0) except for a few cases where abnormalities resulting in overheating were present, and in those cases the nitrogen-to-oxygen ratio was much higher and mass spectrographic analysis showed that the oxygen concentration had in fact been lowered.

The oxygen concentration in the coolant gas of a large hydrogen-cooled generator, or preferably the nitrogen-to-oxygen ratio, can thus be used as an accurate indication of the presence of incipient faults either thermal or electrical. This method of detecting such faults provides far better protection than methods based on particulation of organic material, which are less accurate and reliable and are limited to detecting overheating of organic materials. A change in the nitrogen-oxygen ratio indicates overheating of any materials or components in a machine including both organic insulation and metallic elements, and has the further advantage of also indicating arcing or corona faults which also cause oxidation reactions even if the heating is highly localized or not excessive. Thus a better and more accurate method for detection of incipient faults is provided than has heretofore been available. This method also has the further advantage that a simple way exists for checking the indication of a fault. This can readily be done by feeding additional air into the generator to increase the oxygen concentration, and then observing the time required for the nitrogen-to-oxygen ratio to again increase. This provides an accurate and easily applied means of checking the existence of the incipient fault.

The nitrogen-to-oxygen ratio can be determined in any desired or known manner, and may be either continuously monitored or observed at regular intervals. Any suitable means for making such determinations may be utilized. The mass spectrometer and the gas chromatograph are frequently used for making such gas analyses and are readily available. Either of these devices could therefore be used.

A preferred means for determining the nitrogen-oxygen ratio is shown in FIG. 2 which also employs known and readily available equipment. In this method, the well-known conventional purity meter which is commonly used with hydrogen-cooled generators is utilized. Such meters consist of a fan or blower driven at constant speed. The hydrogen atmosphere in the generator is continuously sampled and supplied to this blower. The pressure rise across the blower, when compensated for ambient temperature and pressure variations, gives a direct indication of the gas density and thus of the concentration of air in the hydrogen-air mixture. When the percentage of air in the hydrogen is known, the heat content of the gas, resulting from controlled combustion of hydrogen and oxygen, provides a measure of the oxygen content of the gas. This heat content can be measured by conventional catalytic or solid electrolyte combustion gages which are well known and readily available devices.

The nitrogen-to-oxygen ratio in the generator atmosphere can accordingly be determined as shown diagrammatically in FIG. 2. A conventional purity meter 20 is there shown which receives gas from the generator through a sampling line 21 and returns it to the generator through a second sampling line 22. As previously described, the meter 20 comprises a blower driven at constant speed and the pressure rise across the blower is a measure of the gas density and, therefore, of the content of air in the gas. This pressure difference is applied to a meter 23 which may be calibrated directly in percentage of air and which is a usual part of the conventional hydrogen control system. For the purposes of the present invention, the oxygen content of the gas is measured by means of a conventional combustion gage 24, which may be of either of the types mentioned above or of any suitable type. The gage 24 takes a small amount of gas from either of the sampling lines 21 or 22 and determines the percentage oxygen content by measuring the heat content. The gage may be directly calibrated to show the oxygen content in percentage as indicated at 25. As long as the air has its normal ratio of nitrogen-to-oxygen, the ratio of the percentage of oxygen in the gas to the percentage of air in the gas will remain constant even though the actual amount of air present in the gas may vary from time-to-time. The ratio of the readings of the meters 23 and 25 will, therefore, remain constant under normal conditions. A marked reduction of this ratio, however, indicates a reduction in the amount of oxygen, or an increase in the nitrogen-oxygen ratio, and thus indicates the presence of an incipient fault condition. The ratio of the readings of the two meters can be determined by visual observation, or may be calculated automatically and shown in a visual display of any type, or utilized to actuate an alarm or produce any other type of response that may be desired. The existence of an incipient fault is thus indicated so that remedial action can be taken before any serious fault can develop.

It should now be apparent that a method for detecting incipient faults in a hydrogen-cooled generator has been provided which has many advantages. A fault indication of much greater reliability and accuracy is provided than has heretofore been possible and an indication is obtained for both thermal and electrical faults, and at a lower temperature than has previously been required. The presence of the fault can easily and quickly be checked as previously described, and equipment which is already provided for most generators is utilized to serve a second function so that the cost is kept low.

What is claimed is:

1. A method for detecting incipient faults in a dynamoelectric machine having a housing filled with a coolant gas comprising hydrogen containing not more than 10% air, said method consisting of measuring the free oxygen concentration of said coolant gas under normal conditions, monitoring the free oxygen content of said coolant gas during operation of said dynamoelectric machine and detecting any substantial reaction of the free oxygen with hydrogen producing a concentration of free oxygen below that measured under said normal condition.

2. A method as defined in claim 1 in which the oxygen content of the coolant gas is monitored by measuring the ratio of oxygen to another component of air in the gas.

3. A method as defined in claim 1 in which the oxygen content of the coolant gas is monitored by measuring the ratio of nitrogen-to-oxygen in the gas.

4. A method as defined in claim 3 in which the ratio of nitrogen-to-oxygen is determined by measuring the content of air in the coolant gas, measuring the oxygen content of the gas, and detecting any substantial change in the ratio of the oxygen content to the air content.

5. In combination, a dynamoelectric machine having a housing filled with a coolant gas comprising at least 90% hydrogen containing a predetermined free oxygen concentration for normal conditions, and means for monitoring the free oxygen content of said coolant gas and detecting any substantial reaction of the free oxygen with hydrogen producing a concentration of free oxygen below that for said normal conditions.

6. The combination defined in claim 5 in which said means for monitoring the oxygen comprises means for determining a decrease in concentration of said oxygen in the nitrogen-to-oxygen ratio present in the coolant gas.

7. The combination defined in claim 6 in which said monitoring means includes means for measuring the content of air in the coolant gas, and means for measuring the oxygen content of said air.

8. The method as defined in claim 1 including means for checking said detected incipient faults comprising: mixing additional air with said coolant gas; monitoring the free oxygen content of said coolant gas; and detecting any substantial repeated combination of the free oxygen with other elements.

* * * * *